(12) United States Patent
Tröllsch

(10) Patent No.: US 9,207,170 B2
(45) Date of Patent: Dec. 8, 2015

(54) GAS DETECTOR SYSTEM

(71) Applicant: DRÄGER SAFETY AG & CO. KGAA, Lübeck (DE)

(72) Inventor: Arne Tröllsch, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 0 days.

(21) Appl. No.: 14/386,938

(22) PCT Filed: Apr. 10, 2013

(86) PCT No.: PCT/EP2013/057474
§ 371 (c)(1),
(2) Date: Sep. 22, 2014

(87) PCT Pub. No.: WO2013/153106
PCT Pub. Date: Oct. 17, 2013

(65) Prior Publication Data
US 2015/0041660 A1   Feb. 12, 2015

(30) Foreign Application Priority Data

Apr. 14, 2012   (DE) .......................... 10 2012 007 561

(51) Int. Cl.
*G01N 21/3504* (2014.01)
*G01N 21/31* (2006.01)
*G01N 33/00* (2006.01)

(52) U.S. Cl.
CPC .......... *G01N 21/3504* (2013.01); *G01N 21/314* (2013.01); *G01N 33/0031* (2013.01); *G01N 33/0062* (2013.01); *G01N 2021/3513* (2013.01)

(58) Field of Classification Search
CPC ............ G01N 21/3504; G01N 21/314; G01N 33/0031; G01N 33/0062; G01N 2021/3513
USPC ......................................................... 250/353
See application file for complete search history.

(56) References Cited

U.S. PATENT DOCUMENTS

| | | | | |
|---|---|---|---|---|
| 3,370,502 A | * | 2/1968 | Wilks, Jr ........................ 356/133 |
| 4,560,873 A | * | 12/1985 | McGowan et al. ....... 250/339.09 |
| 4,681,454 A | * | 7/1987 | Breemer ........................ 356/402 |
| 5,091,649 A | * | 2/1992 | Rantala ......................... 250/343 |
| 5,163,332 A | * | 11/1992 | Wong ......................... 73/863.23 |
| 5,252,828 A | * | 10/1993 | Kert et al. ................. 250/339.13 |
| 5,254,858 A | * | 10/1993 | Wolfman et al. ......... 250/339.06 |
| 5,339,155 A | * | 8/1994 | Partridge et al. .............. 356/419 |
| 5,591,975 A | | 1/1997 | Jack et al. |

(Continued)

*Primary Examiner* — Marcus Taningco
*Assistant Examiner* — Djura Malevic
(74) *Attorney, Agent, or Firm* — McGlew and Tuttle, P.C.

(57) ABSTRACT

A gas detector system includes a transmitter (1), which has a light source (3), which emits an analytical light beam (5). A transmitter lens assembly (7), to focus the analytical light beam (5) in an emission direction (9), includes a receiver (19, 19') with a receiver lens assembly (21), defining a receiver focal point (27, 27') and a receiver axis (23). A light mixing rod (29) defines a first rod axis (35) that extends from an inlet end (31), pointing toward the receiver lens assembly (21), to an outlet end (33) facing an analytical detector (39) and a reference detector (45). An analytical filter (43, 43') is arranged in front of the analytical detector (39) as viewed from the receiver lens assembly (21). A reference filter (49, 49') is arranged in front of the reference detector (45) as viewed from the receiver lens assembly (21).

16 Claims, 6 Drawing Sheets

(56) References Cited

U.S. PATENT DOCUMENTS

| | | | |
|---|---|---|---|
| 5,637,872 A * | 6/1997 | Tulip ........................... 250/338.5 |
| 5,677,762 A | 10/1997 | Ortyn et al. |
| 5,679,957 A * | 10/1997 | Durham et al. ............... 250/373 |
| 6,097,034 A * | 8/2000 | Weckstrom et al. ........ 250/495.1 |
| 6,444,985 B1 * | 9/2002 | Mori et al. ................ 250/339.13 |
| 6,469,303 B1 * | 10/2002 | Sun et al. ....................... 250/343 |
| 6,538,251 B1 * | 3/2003 | Weckstrom et al. ........... 250/343 |
| 6,538,728 B1 * | 3/2003 | Stolle et al. .................... 356/437 |
| 7,291,839 B1 * | 11/2007 | Demers et al. .............. 250/341.1 |
| 7,928,394 B1 * | 4/2011 | Richer ........................... 250/343 |
| 2003/0191393 A1 | 10/2003 | Ridder et al. |
| 2005/0061778 A1 * | 3/2005 | Arakawa et al. ............ 219/121.6 |
| 2007/0120057 A1 * | 5/2007 | Tsai et al. ................... 250/338.1 |
| 2008/0185524 A1 * | 8/2008 | Kanstad ..................... 250/338.5 |
| 2011/0268453 A1 | 11/2011 | Fest et al. |
| 2012/0161022 A1 * | 6/2012 | Thomson et al. .............. 250/372 |

* cited by examiner

GAS DETECTOR SYSTEM

CROSS REFERENCE TO RELATED APPLICATIONS

This application is a United States National Phase Application of International Application PCT/EP2013/057474 filed Apr. 10, 2013 and claims the benefit of priority under 35 U.S.C. §119 of German Patent Application 10 2012 007 561.8 filed Apr. 14, 2012, the entire contents of which are incorporated herein by reference.

FIELD OF THE INVENTION

The present invention pertains to a gas detector system with a transmitter with a light source, by which an analytical light beam is emitted, and with a transmitter lens assembly, which is designed to focus the analytical light beam along an emission direction, as well as with a receiver with an analytical detector and with a reference detector.

BACKGROUND OF THE INVENTION

The analysis of gas mixtures has acquired increasing significance in both process control engineering and monitoring engineering as well as environmental analyses. In addition, the requirements imposed on such measuring systems for gas analysis in terms of measuring sensitivity, long-term stability, selectivity as well as the requirements in terms of the intervals between maintenance procedures and the service life of the measuring systems have been increasing with the increasing degree of automation in industry and environmental monitoring. To recognize gases being discharged in case of defects as quickly as possible, for example, in environmental analyses or in the monitoring of larger industrial plants, it is desirable to cover the areas to be monitored at as close intervals as possible and over as large an area as possible. A large number of sensors, which have locally narrowly limited sensitivity and may be connected with one another via data links, may be used for this.

Far more advantageous and effective are, however, optically imaging gas sensors, in which the light emitted is directed over long measuring sections and wherein the absorption of the light represents the gas species-specific measured effect. Such systems make it possible to obtain data on the mean gas concentration in the measured section and to monitor larger areas.

Such gas detector systems, with a transmitter, with a receiver and with a free measured section located between them, along which the gas composition or the concentration of a certain gas component is detected, are usually called open-path systems, wherein the distance between the transmitter and the receiver, i.e., the length of the free measured section, may be in the range of 200 m. This makes it necessary for the transmitter and the receiver to be exactly aligned with one another in order for the analytical light beam emitted by the transmitter to also actually reach the optical system of the receiver to the full extent. However, even if this is the case, it is, moreover, necessary for the analytical light beam to exactly reach the receiver at the correct site in order to ensure that the highest possible intensity can be detected in the detectors present in the receiver. Consequently, if the transmitter and/or the receiver are not correctly aligned, the system may not operate reliably or with the desired sensitivity.

Such a gas detector system with an open measured section with a laser as the light source and with a receiving element in a common housing is known, for example, from U.S. Pat. No. 5,339,155, in which it is described that light is directed and emitted by means of a semitransparent mirror and an obliquely positioned mirror onto a concave mirror and from there as a parallel beam through the open measured section onto a remote reflector and is reflected from there back to the receiving element into the housing.

An arrangement with an optical gas-measuring system with an open measured section, with a transmitter and with a receiver, is known from U.S. Pat. No. 6,538,728, in which a measuring light source in the transmitter emits an analytical beam into an open measured section, the analytical beam passes through the open measured section, and a detector in the receiver records the analytical beam. A gas concentration of a target gas is determined on the basis of the analytical beam recorded by the detector. Furthermore, two optical or telemetric communication channels, in which a bidirectional data exchange is made possible between the transmitter and the receiver, is disclosed in U.S. Pat. No. 6,538,728. This data exchange makes it possible to obtain information concerning the alignment of the transmitter and receiver at the transmitter and the receiver from the received data by means of data communication and thus to recognize a maladjustment and to support a correction of the adjustment.

Furthermore, arrangements in which an adjusting device with a measuring element 111 is provided for detecting the maladjustment in the alignment, especially tilting of the optical axes 106 of the transmitter 105 and receiver 103 in relation to one another, are known from the state of the art (FIGS. 1a and 1b). The transmitter 105 comprises a light source and a lens assembly 113, and the receiver 103 has a lens assembly 116, a measuring element 111 and a detector 114. Such an arrangement is used by the applicant for gas measurement in open areas, wherein the measuring element 111 is designed as a circular ring, which is arranged at a preset distance from the 114 and on which a number of light-sensitive sensors are arranged at uniformly spaced locations over the entire circumference. This circular ring acts as an apertured diaphragm, which transmits an inner core beam 109 of the parallel light bundle emitted by the light source of the transmitter 105 to the detector 114 and captures an outer marginal beam of the parallel light bundle on the ring itself and on the light-sensitive sensors arranged thereon and thus does not permit it to reach the detector 114. In the adjusted state of the receiver 103, all light-sensitive sensors detect the same intensity. However, some light-sensitive sensors detect no light or little light in case of maladjustment of the receiver 103, and information on the maladjustment can be obtained from this distribution. However, this arrangement of the measuring element 111 leads to an additional loss of light, because part of the light emitted by the transmitter 105, which light is needed for the adjustment of the transmitter and receiver, fails to reach the detector 114 and thus cannot make any further contribution to the measurement at the detector 114.

Moreover, the problem arises, in principle, that the sensitivity is not constant in the detectors being used as a function of the location on the detector surface but increases towards the edge. Consequently, if the beam spot falling on the detector is smaller than the detector surface or the detector surface is not illuminated homogeneously, the measured intensity changes even if there is a shift of the beam spot. However, since the ratio of the intensities measured at the analytical detector and at the reference detector is used as an indicator for the gas concentration, even a slight change in the adjustment of the transmitter or receiver may lead to a significant change in the measured signal.

Another problem is that the transmission range or the cutoff wavelength of the bandpass filters used in open-path systems is a function of the angle of incidence. The change in the respective cut-off wavelengths is especially great if the angle of incidence onto the filter is in the range of 45°. Since such an arrangement is frequently used in gas detector systems to reflect the part that is not transmitted by the filter to another measurement arrangement, incorrect adjustment may soon cause a displacement of the spectral transmission range or the cut-off wavelength here as well, and consequently likewise a changed measurement result.

If the transmitter and receiver are aligned with one another after an approximate adjustment such that the detectors in the receiver "see" the analytical light beam, there still are two possibilities of how the transmitter and receiver are misaligned with one another. On the one hand, the transmitter may be slightly tilted in relation to the connecting line between the transmitter and the receiver, and, on the other hand, it is also conceivable that the receiver is tilted in relation to this connecting line. It is therefore desirable if the transmitter and the receiver are designed such that it is readily possible to identify whether one or both of the above-mentioned cases occur.

SUMMARY OF THE INVENTION

The gas detector system should be designed especially such that it can be aligned in a simple manner, possibly without the use of complicated optical systems.

Based on the state of the art, an object is therefore to provide a gas detector system, in which incorrect alignments have, within a tolerance range, only a very little effect on the intensity detected by the analytical detector.

This object is accomplished according to the present invention by a gas detector system comprising a transmitter with a light source, by which an analytical light beam is emitted, and with a transmitter lens assembly, which is designed to focus the analytical light beam along an emission direction, and a receiver with a receiver lens assembly, which defines a receiver focal point and a receiver axis, with a first light mixing rod, which has a first inlet end and a first outlet end and defines a first rod axis extending from the first inlet end to the first outlet end, wherein the first inlet end points towards the receiver lens assembly, with an analytical detector and a reference detector. The analytical detector is arranged on the side of the first outlet end pointing away from the receiver lens assembly. An analytical filter is arranged in front of the analytical detector as viewed from the receiver lens assembly. A reference filter is arranged in front of the reference detector as viewed from the receiver lens assembly.

A light mixing rod in the sense of the present invention is defined as a body or hollow body, which extends along a rod axis, is symmetrical thereto and whose outer wall is designed such that radiation entering the interior of the body or hollow body through the inlet end is reflected at the circumferential wall and is thus held in the interior of the body. This causes radiation entering at the inlet end to leave the body or hollow body at the outlet end as a beam with an intensity that is homogeneous over the cross-sectional area of the beam when the focal point of the radiation entering at the inlet end is located in the plane of the inlet end or at a short distance behind it in the interior of the body or hollow body. Such light mixing rods are known from projectors.

The use of a light mixing rod in the receiver makes it possible to bundle the radiation arriving from the transmitter, which falls on the receiver lens assembly, such that the beam spot falling on the analytical detector is illuminated homogeneously. If this beam spot is larger than the surface, a slight maladjustment of the receiver, which does not cause the beam spot to move compared to the optimal position in which the detector is located in the center of the beam spot, does not lead to a change in the signal sent by the detector. As a result, the tolerance range within which the receiver may be maladjusted is increased compared to conventional systems.

The receiver lens assembly preferably has a field lens here, which is arranged in front of the inlet end. This causes the light falling into the light mixing rod to be collimated such that the beam spot formed after the light mixing rod is illuminated very homogeneously.

The focal point is preferably located within the first light mixing rod, which is associated with the advantage that it cannot happen that impurities could occur in areas in which the beam is strongly collimated. The consequence of this could be that great losses of intensity would occur. This risk would be present especially if the focal point were located on a surface of the light mixing rod at the inlet end. In addition, the overall length is reduced in case of such a preferred design.

According to a preferred embodiment, the first beam axis extends along the receiver axis, and the first outlet end has a prism assembly for splitting a beam leaving the first light mixing rod into a first beam and a second beam, wherein the first beam propagates along a first direction and the second beam along a second direction, and the first and second directions extend at an angle to the first rod axis, wherein the analytical detector is arranged along the first direction, wherein the reference detector is arranged along the second direction, wherein the analytical filter is arranged between the analytical detector and the first outlet end, and wherein the reference filter is arranged between the reference detector and the first outlet end.

One light mixing rod is sufficient in such an arrangement, and the prism assembly is used to image the homogeneously illuminated beam spot on both the analytical detector and the reference detector. It is not necessary here to split the beam falling into the receiver by means of a cut-off filter, and the analytical beam and the reference beam will now extend each along separate paths, possibly still through separate light mixing rods.

Corresponding bandpass filters are arranged in front of the respective in this preferred embodiment, but the transmission ranges of these bandpass filters differ from one another in order to obtain and detect the wavelength range with the absorption bands in question, on the one hand, and a section of the beam without this band, on the other hand.

Finally, a receiver light source may be arranged on the receiver axis on the side of the outlet end facing away from the receiver lens assembly. Light that is emitted by this receiver light source will then fall on the transmitter. If the latter has a filter, which is arranged between the transmitter lens assembly and the light source and which reflects light falling on the transmitter lens assembly against the emission direction onto a first position-sensitive detection means provided in the transmitter, the signal of this detection means may be used to determine how the transmitter is tilted in relation to the connecting line between the transmitter and the receiver. The alignment of the transmitter can be greatly simplified hereby.

Furthermore, it is preferred if light-sensitive sensors, whose light-sensitive areas point towards the interior of the light mixing rod, are arranged at the circumferential wall extending between the inlet end and the outlet end of the first light mixing rod at spaced locations in the circumferential direction. If the focal point of the beam falling on the inlet end of the first light mixing rod is lot located on the rod axis, but is laterally offset in relation thereto, more light falls on this side onto the corresponding light-sensitive sensor, so that this above-described arrangement makes it possible to determine the incorrect alignment of the receiver on the basis of the signals of the sensors. A possibly existing tilting of the receiver in relation to the connecting line between the transmitter and the receiver can thus also be determined in a simple manner without the use of optical instruments.

It is especially preferred in this connection if the first light mixing rod has a polygonal cross section as viewed at right angles to the first rod axis. Greater homogenization of the beam is achieved in case of such a symmetry, which is lower than in case of a round cross section, and the sensors can be arranged at the same time in a simple manner.

In an alternative embodiment, the receiver has a second light mixing rod, which has a second inlet end and a second outlet end, and defines a second rod axis extending from the second inlet end to the second outlet end, wherein the second inlet end is arranged closer to the receiver lens assembly as viewed in the direction of a beam falling into the receiver, wherein the first and second rod axes extend at an angle to one another, wherein the reference detector is arranged on the side of the second outlet end pointing away from the receiver lens assembly as viewed in the direction of a beam falling into the receiver, wherein the analytical filter is arranged between the first inlet end and the receiver lens assembly, wherein the analytical filter is aligned such that light falling on the analytical filter along the receiver axis, which light is not transmitted, is reflected onto the second inlet end along the rod axis, and wherein the reference filter is arranged between the receiver lens assembly and the analytical filter.

Such an arrangement makes it possible to use common reference and analytical filters for the analytical detector and the reference detector.

In addition, the light mixing rods may have a simpler design in this case and do not require an expensive prism assembly at the outlet end. As a result, the intensity detected in the detectors is also higher, in principle, which does, in turn, increase the probability of detection of the gas component to be detected.

The first rod axis is directed along the receiver axis in a preferred embodiment, while the second rod axis extends at an angle, preferably at right angles, to the receiver axis. The arrangement can be embodied in a simple manner with only a small number of optical elements in this case. In particular, the further optical elements of the receiver can now be easily adjusted during assembly.

It is also possible with such an arrangement that the reference filter is directed such that light falling on the reference filter along the receiver axis, which light is not transmitted, is reflected onto a second position-sensitive detection means provided in the receiver. The signal in the position-sensitive detection means can be used in this case to determine whether the receiver is aligned correctly in relation to the connecting line between the transmitter and the receiver.

Furthermore, it is advantageous in the above-described preferred embodiment if the optical path lengths between the receiver lens assembly and the first light mixing rod and between the receiver lens assembly and the second light mixing rod are selected to be such that the focal point of the lens assembly of the receiver is located within the first and second light mixing rods. This is, in turn, associated with the advantage that considerable losses of intensity cannot be caused at the detectors even by low impurity levels in the interior of the receiver.

It is advantageous, furthermore, if the reference filter is designed as a bandpass filter and the analytical filter as a cut-off filter and the lower threshold wavelength of the bandpass filter is lower than the cut-off wavelength of the cut-off filter. Only the light emitted by the light source, which contains the spectrum relevant for the measurement, can be selected in this manner by the bandpass filter. The cut-off filter is subsequently used to transmit only the light that contains the absorption lines in question to the analytical detector.

To prevent the beam spot falling on the detectors from becoming too large, so that the entire intensity will reach the detectors, but the system is nevertheless sufficiently tolerant for errors, it is preferred for the light mixing rods to have a conical design tapering towards the outlet end.

Finally, it is especially preferred if the position-sensitive detection means used are designed as CCD, CMOS or quadrant detectors, because they are cost-effective and can be reliably analyzed.

The present invention will be explained below on the basis of drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
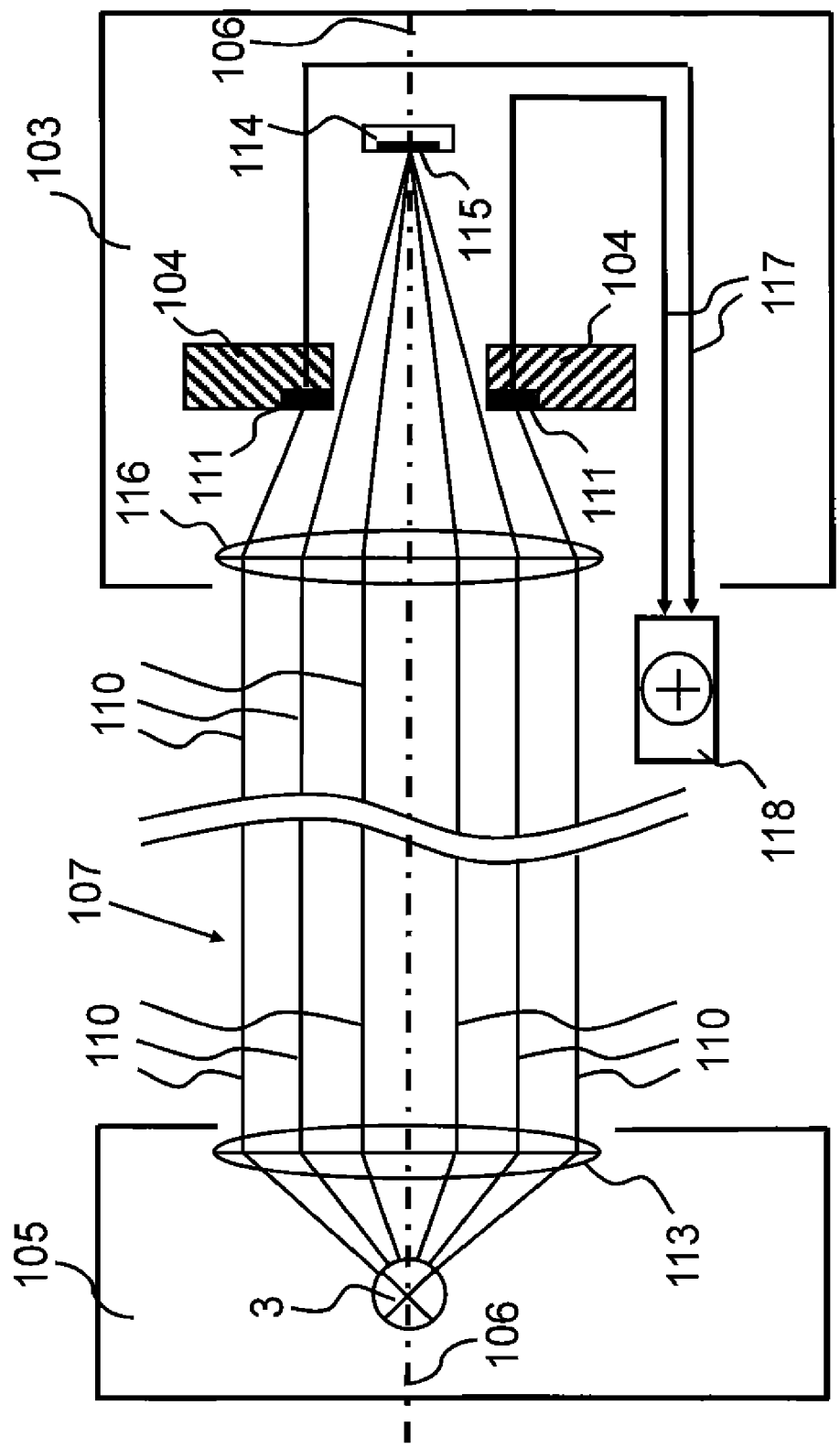
FIG. 1a is a view of a portion of a system according to the state of the art.
Figure 1B:
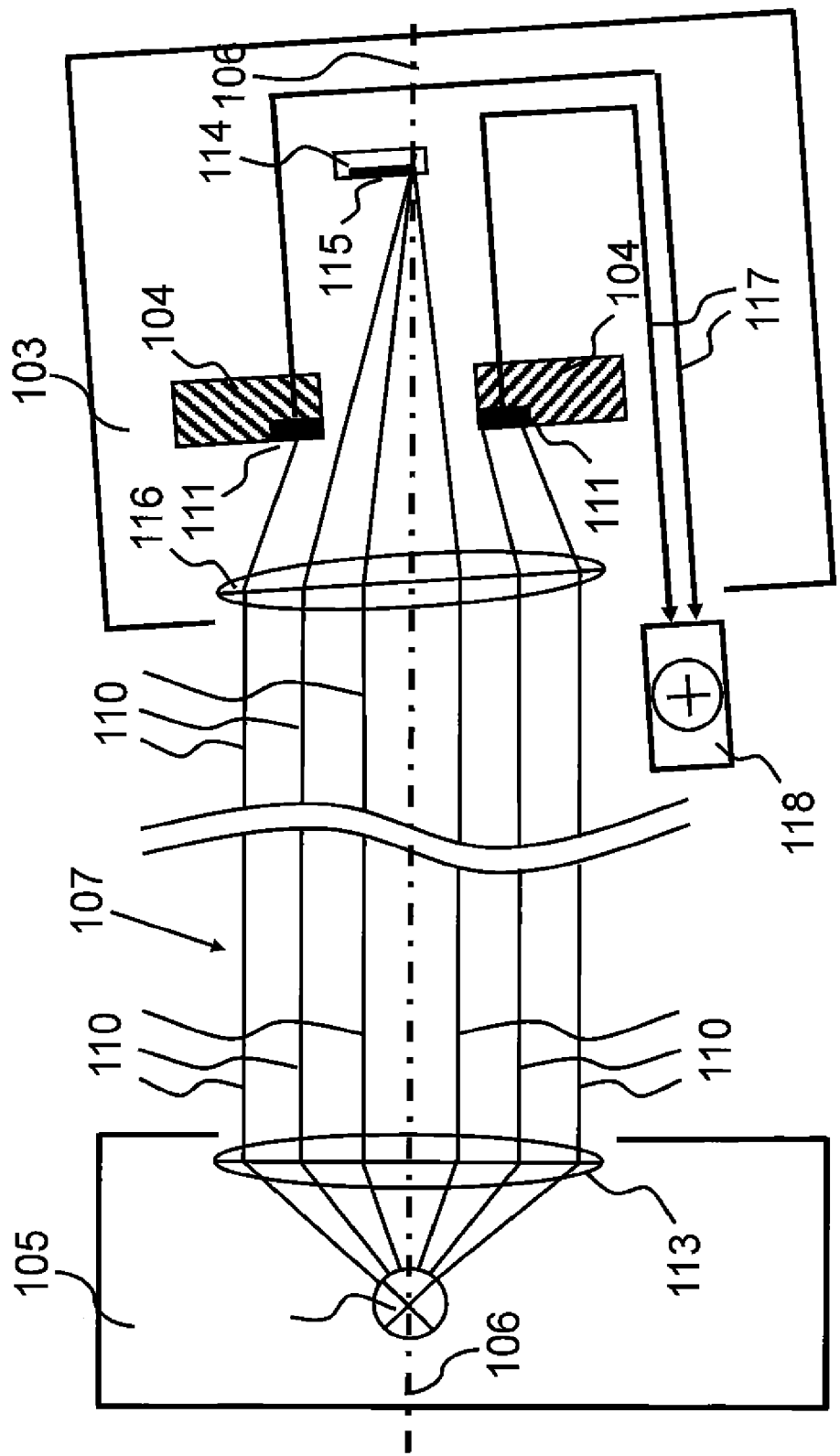
FIG. 1b is a view of another portion of a system according to the state of the art.
Figure 2:
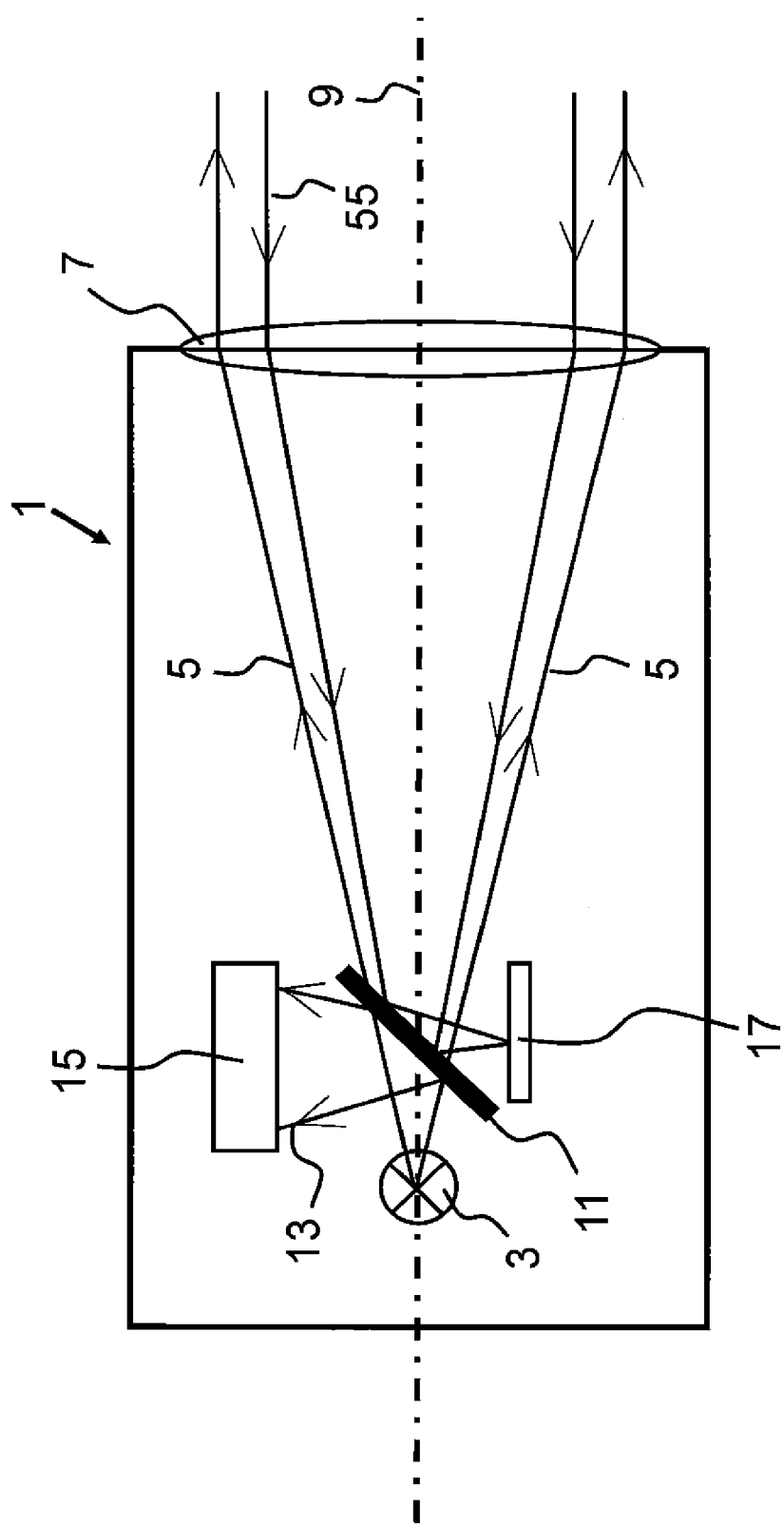
FIG. 2 is a view showing a transmitter of a first exemplary embodiment according to the present invention.

Referring to the drawings in particular, as can be recognized from FIG. 2, the transmitter 1 according to a first exemplary embodiment of a gas detector system according to the present invention has a light source 3, by which an analytical light beam 5 is emitted. Furthermore, a transmitter lens assembly 7, which comprises only one lens in this case, and with which the light emitted by the light source 3 is collimated along an emission direction 9, is provided in the transmitter 1.

In addition, a color splitter 11 is arranged in the transmitter 1 such that light emitted by the light source 3 falls on the color splitter 11 before it reaches the transmitter lens assembly 7. This color splitter acts such that infrared light passes unhindered through the color splitter 11 and this forms the analytical light beam 5, while visible light 13 is reflected by the color splitter 11 and cast into a beam dump 15.

The side of the color splitter 11 facing away from the light source 3 and pointing towards the transmitter lens assembly 7 is designed such that visible light falling on this side is reflected. The color splitter 11 is aligned here with the transmitter lens assembly 7 such that light falling on the transmitter lens assembly 7 along the emission direction 9 is cast by the color splitter 11 onto a position-sensitive detector 17, which is likewise arranged in the transmitter 1 and forms a position-sensitive detection means.

Figure 3:
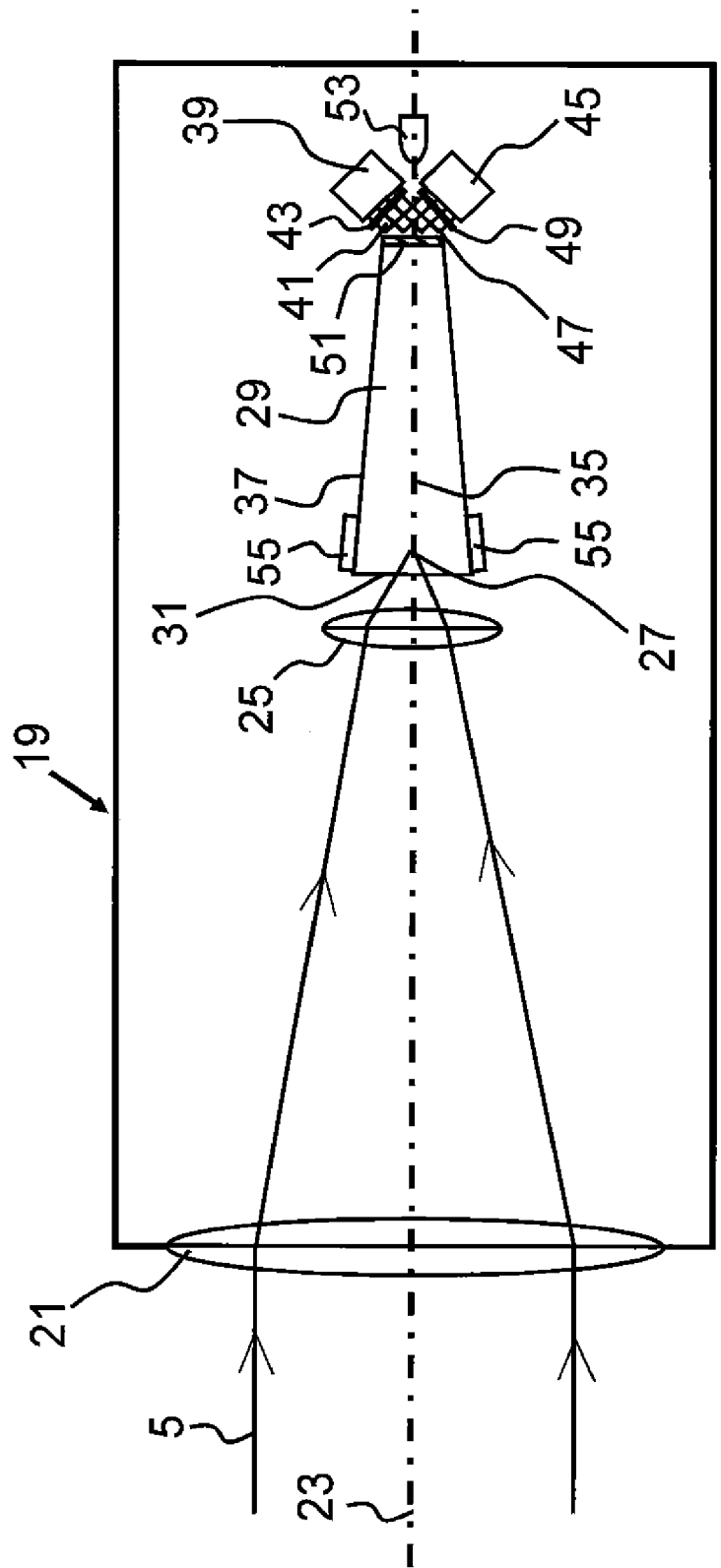
FIG. 3 is a vie showing the receiver according to the first exemplary embodiment according to the present invention.

As is apparent from FIG. 3, the receiver 19 according to the first exemplary embodiment has a receiver lens assembly 21, which is likewise formed from an individual lens in this exemplary embodiment and which defines a receiver axis 23. Likewise on the receiver axis 23 is arranged a field lens 25. This is used to further collimate the beams already focused by the receiver lens assembly 21. In addition, a receiver focal point 27, which is located on the receiver axis 23, is defined by the receiver lens assembly 21.

Furthermore, a first light mixing rod 29, which has a first inlet end 31 as well as a first outlet end 33, is provided in the receiver 19 on the receiver axis 23. The first rod axis 35, which is defined by the light mixing rod 29 and which is aligned with the receiver axis 23 in this exemplary embodiment, extends between the first inlet end 31 and the first outlet end 33. As can further be recognized from FIG. 3, the first light mixing rod 29 is arranged such that the receiver focal point 27 is located within the first light mixing rod 29.

A light mixing rod 29 is defined in the sense of the present invention as a body or hollow body extending along the rod axis 35 and having a symmetry therewith, which is transparent and whose circumferential wall 37 is designed such that light falling into the interior of the light mixing rod 29 is reflected at the circumferential wall 37 and is thus held in the interior of the light mixing rod 29. This causes radiation entering at the inlet end 31 to leave the light mixing rod 29 at the outlet end 33 as a beam with an intensity that is homogeneous over the cross section.

The light mixing rod 29 preferably has a polygonal cross section as viewed at right angles to the rod axis 35, and the light mixing rod may taper conically towards the outlet end 33. Greater homogenization of the beam is achieved in case of such a symmetry, which is lower than in case of a round cross section.

Figure 4:
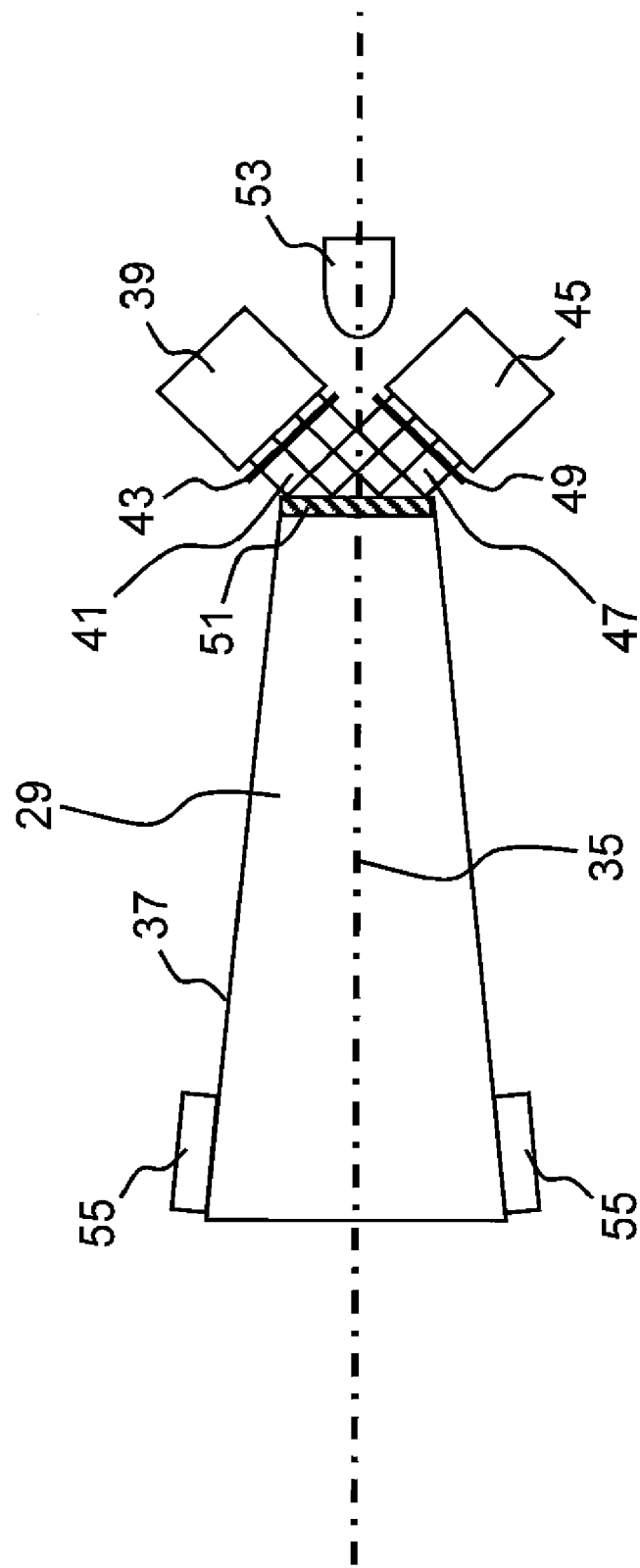
FIG. 4 is a view showing a part of the receiver from FIG. 3 in an enlarged view.

As is apparent from FIGS. 3 and 4, an analytical detector 39 is arranged on the side of the first outlet end 33 of the light mixing rod 29 pointing away from the receiver lens assembly 21, and the analytical detector 39 is arranged along a first direction, along which a first beam 41, which exits from the first outlet end 33 of the light mixing rod 29, propagates. Finally, an analytical filter 43 is provided between the analytical detector 39 and the first outlet end 33.

A reference detector 45 is likewise provided on the side of the first outlet end 33 pointing away from the receiver lens assembly 21, and this detector is arranged along a second direction, along which a second beam 47 exits from the first outlet end 33 of the light mixing rod 29. Finally, a reference filter 49 is also provided between the reference detector 45 and the first outlet end 33. Both the first beam 41 and the second beam 47 or the first and second directions extend at an angle relative to the first rod axis 35 and the receiver axis 23.

To ensure that the first and second beams 41, 47 propagate each at an angle in relation to the receiver axis 23 from the first outlet end 33, a prism assembly 51 is provided for splitting the beam leaving the first light mixing rod 29, which splits this beam into the first and second beams 41, 47. In particular, the prism assembly may be designed such that it has a plurality of individual prisms extending at right angles to the drawing plane and are arranged in parallel to one another.

Both the analytical filter 43 and the reference filter 49 are designed as bandpass filters, but their transmission ranges differ from each other and do not overlap each other.

Finally, it can be recognized from FIGS. 3 and 4 that the receiver 19 has a receiver light source 53, which is located on the receiver axis 23 and may be designed as a light-emitting diode and emits light along the receiver axis 23 in the direction of the receiver lens assembly 21.

Furthermore, it can be determined from FIGS. 3 and 4 that light-sensitive sensors 55 located at spaced locations from one another in the circumferential direction are arranged at the circumferential wall 37 of the light mixing rod 29, and said sensors 55 point towards the interior of the light mixing rod 29.

The above-described first exemplary embodiment of a gas detector system according to the present invention, which is shown in FIGS. 2 through 4, operates as follows.

An analytical light beam 5 is emitted by the light source 3, and this light beam first passes through the color splitter 11, while visible light 13 is captured in the beam dump 15 without being able to propagate farther in the receiver 1. The analytical light beam 5 is focused by the transmitter lens assembly 7 to a parallel beam, which will then fall onto the receiver lens assembly 21 through the transmitter lens assembly 7, and this bundle will then fall on the receiver lens assembly 21 after passing through the measured section, and if the transmitter 1 and the receiver 19 are aligned with one another such that the emission direction 9 and the receiver axis 23 coincide, this beam will be focused into the receiver focal point 27, which is arranged in the first light mixing rod 29. The incident analytical light beam 5 is homogenized by the first light mixing rod 29 by multiple reflections at the circumferential wall 37, so that the light beam exiting at the first outlet end 33 is homogeneous as viewed over the outlet end 33, i.e., it has a nearly homogeneous intensity as viewed over the surface of the first outlet end.

The prism assembly 51 provided at the first outlet end 33 splits the exiting light into a first beam 41, which falls at first through the analytical filter 43 and then enters the analytical detector 39, and a second beam 47, which falls into the reference detector 45 through the reference filter 49. The transmission range of the analytical filter 43 is selected to be such that the range of the frequency spectrum in which the absorption bands of the gas component to be detected along the measured section is transmitted. The transmission range of the reference filter 49 does not overlap the transmission range of the analytical filter 43, so that the reference detector 45 sends a signal that is independent from the gas concentration in question, while a signal that is dependent on the concentration of the gas component in question along the measured section is sent by the analytical detector 39. The absolute concentration of the gas component can then be inferred from the ratio of the two signals.

If the beam spot generated by the first and second beams 41, 47 on the detectors 39, 45 is larger than the respective detector surface, a slight maladjustment of the receiver 19, at which the beam spot in relation to the optimal position, in which the detectors 39, 45 are located in the center of the beam spot, does not lead to a change in the signals sent by the detectors 39, 45, because the beam spot is always illuminated homogeneously because of the light mixing rod 29. The tolerance range within which the receiver 19 may be maladjusted is increased hereby compared to conventional systems. Furthermore, a single light mixing rod 29 is sufficient in case of the above-described design of the receiver 19, and the prism assembly 51 will then be used to image the homogeneously illuminated beam spot on both the analytical detector 39 and the reference detector 45.

It can be determined by means of the sensors 55 arranged at the first light mixing rod 29 whether the receiver axis 23 is tilted in relation to the connecting line between the transmitter 1 and the receiver 19. The intensities detected by the 55 are compared now, and if one of the intensities detected is higher than the others, this indicates that the receiver axis 23 is tilted in the direction of this sensor 55 in relation to the connecting line. The receiver 19 can then be readjusted correspondingly.

Finally, an adjusting beam 55, which is first homogenized by the light mixing rod 29 and is subsequently converted by the receiver lens assembly 21 into a parallel beam 55, which falls through the transmitter lens assembly 7 into the transmitter 1 and is reflected by the color splitter 11 onto the position-sensitive transmitter detector 17, can be generated by means of the receiver light source 53. It can be determined based on the position detected by this detector 17 whether the emission direction 9 does indeed coincide with the connecting line between the transmitter 1 and the receiver 19 or is tilted in relation hereto.

Thus, it is guaranteed with this first exemplary embodiment of a gas detector system, on the one hand, based on the light mixing rod 29, that a homogeneous beam is generated at the outlet end 33 of the light mixing rod 29, which beam will then fall on the detectors 39, 45, while a slight maladjustment has no effect on the signal sent by the 39, 45, because the beam is homogeneous. Furthermore, the sensors 55 as well as the receiver light source 53 together with the transmitter detector 17 permit a simple adjustment of the gas detector system, which adjustment may possibly be automated.

Figure 5:
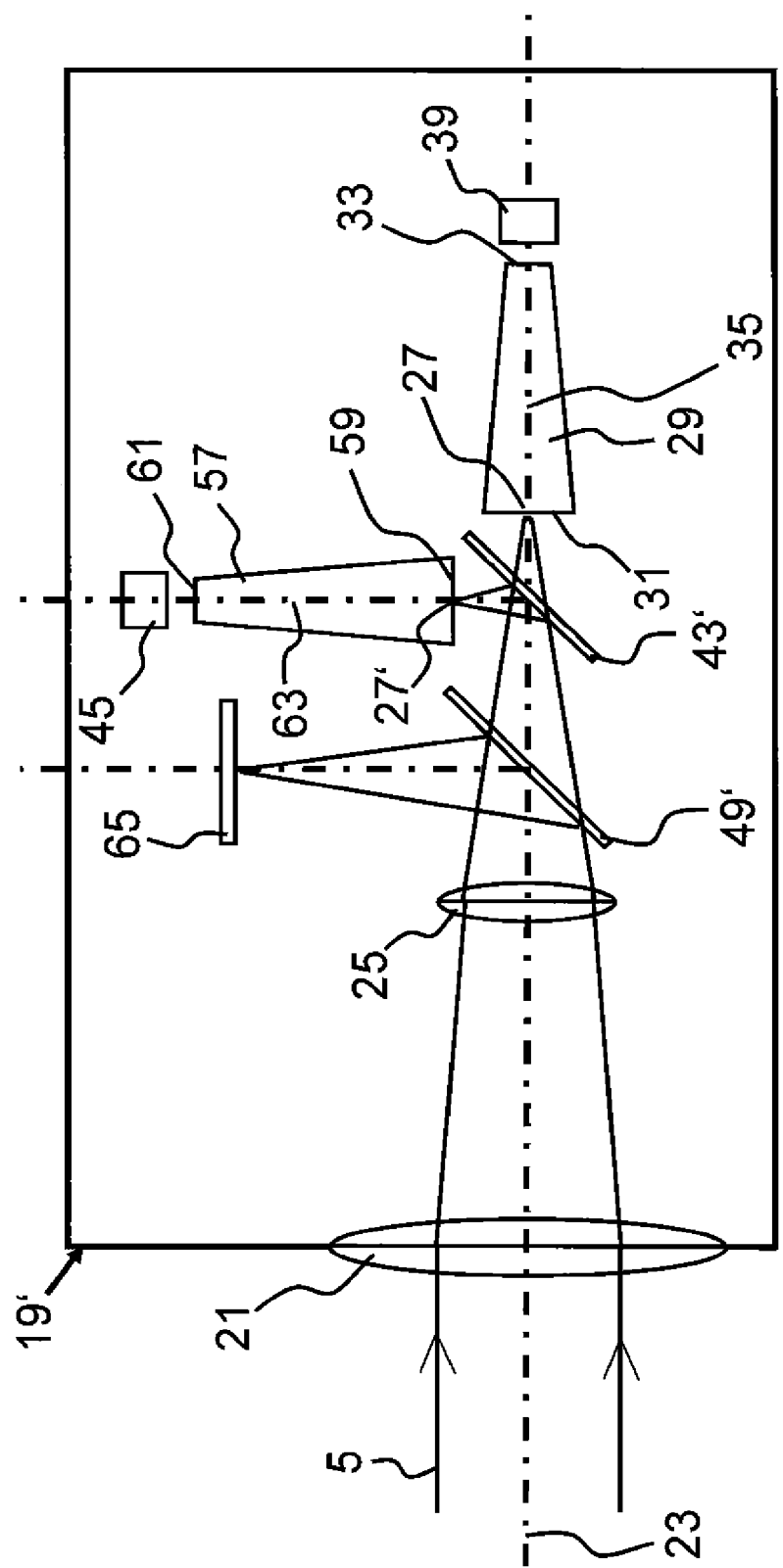
FIG. 5 is a view showing the receiver according to the second exemplary embodiment according to the present invention.

FIG. 5 shows a second exemplary embodiment of a receiver 19', wherein this receiver 19' likewise has a receiver lens assembly 21, which defines a receiver axis 23 and focuses the incident analytical beam 5 into a receiver focal point 27, 27' together with a field lens 25. A receiver focal point 27 is located here in a first light mixing rod 29, which has, in turn, a first inlet end 31 and a first outlet end 33 as well as a first rod axis 35 extending between them. Furthermore, an analytical detector 39 is provided in the receiver 19' on the side of the first outlet end 33 pointing away from the receiver lens assembly 21.

A second light mixing rod 57, which analogously has a second inlet end 59 and a second outlet end 61 as well as a second rod axis 63 extending between them, is also provided in this exemplary embodiment besides the first light mixing rod 29. The light mixing rods 57 have a design similar to that of the first light mixing rod 29 according to the first exemplary embodiment of a receiver 19, i.e., they have a polygonal cross section and taper conically towards the outlet ends 33, 61.

As can also be recognized, the first rod axis 35 and the second rod axis 63 are arranged at right angles to one another in this exemplary embodiment, and the first rod axis 35 extends along the receiver axis 23. However, it is also conceivable that the rod axes 35, 63 extend at an angle that differs from 90°.

An analytical filter 43', through which passes the part of the analytical beam 5 that contains the absorption bands of the gas component to be analyzed, is arranged in the intersection of the extension of the rod axes 35, 63 beyond the respective inlet end 31, 59, while the analytical filter 43' reflects the rest of the analytical beam 5 in the direction of the second light mixing rod 57. In particular, the analytical filter 43' may be designed as a cut-off filter, whose cut-off wavelength, i.e., the wavelength above which the transmission increases, is located directly in front of the absorption bands.

A reference detector 45, with which the light reflected at the analytical filter 43' and homogenized in the second light mixing rod 57 is detected. It is provided on the side of the second outlet end 61 of the second light mixing rod 57 that points away from the receiver lens assembly 21 as viewed in the direction of a beam falling into the receiver 19'.

The light mixing rods 29, 57 are arranged in this exemplary embodiment as well such that the optical wavelengths between the receiver lens assembly 21 and the first light mixing rod 29 and between the receiver lens assembly 21 and the second light mixing rod 57 are each selected to be such that the focal point 27, 27' is located within the first and second light mixing rods 29, 57.

Finally, the receiver 19' has yet another reference filter 49', which is arranged between the receiver lens assembly 21 and the analytical filter 43'. The reference filter 49' is designed as a bandpass filter and transmits the wavelength range in which the absorption bands in question are located, as well as a range in front of that. The rest of the light is reflected. The reference filter 49' is aligned such that light falling on it along the receiver axis 23 and not transmitted falls on a second position-sensitive detection means, namely, a receiver detector 65.

This second exemplary embodiment of a receiver 19' operates as follows. The incident analytical beam 5 is cast by the receiver lens assembly 21 through the partially reflecting analytical filter 43' into both the first light mixing rod 29 and the second light mixing rod 57, the light with the absorption bands in question entering the first light mixing rod 29 and being homogenized therein such that a homogeneous beam spot reaches the analytical detector 39. The part that contains no absorption band is similarly cast into the reference detector 45 in a homogeneous manner. No expensive prism assembly is needed in this design at the outlet end of a light mixing rod, and the intensity detected in the detectors 39, 45 is, in principle, higher, which in turn increases the probability of detection of the gas component to be detected.

The use of light mixing rods 29, 57 likewise leads in this exemplary embodiment to the circumstance that a slight maladjustment of the receiver 19' does not lead to a change in the measurement result if the beam exiting from the light mixing rods 29, 57 at the outlet end 33, 61 has an area that is larger than the sensitive area of the respective detectors 39, 45 and the detector 39, 45 is nevertheless fully irradiated in case of the maladjustment.

Moreover, the light reflected at the reference filter 49' can be used for determining by means of the receiver detector 65 whether the receiver axis 23 actually coincides with the connecting line between the transmitter 1 and receiver 19' or it is somewhat tilted in relation to same.

While specific embodiments of the invention have been shown and described in detail to illustrate the application of the principles of the invention, it will be understood that the invention may be embodied otherwise without departing from such principles.

The invention claimed is:

1. A gas detector system comprising:
   a transmitter comprising a light source, by which an analytical light beam is emitted, and with a transmitter lens assembly, which is designed to collimate the analytical light beam along an emission direction, and
   a receiver comprising a receiver lens assembly, which defines a receiver focal point and a receiver axis, a light mixing rod, which has an inlet end and an outlet end and defines a rod axis extending from the inlet end to the outlet end, wherein the inlet end points towards the receiver lens assembly, an analytical detector and a reference detector, wherein the analytical detector is arranged on a side of the outlet end pointing away from the receiver lens assembly, an analytical filter, which is arranged in front of the analytical detector as viewed from the receiver lens assembly, and a reference filter, which is arranged in front of the reference detector as viewed from the receiver lens assembly.

2. A gas detector system in accordance with claim 1, wherein the receiver lens assembly has a field lens, which is arranged in front of the inlet end.

3. A gas detector system in accordance with claim 1, wherein the focal point is located within the light mixing rod.

4. A gas detector system in accordance with claim 1, wherein:
the rod axis extends along the receiver axis;
the outlet end has a prism assembly for splitting a beam leaving the light mixing rod into a first beam and a second beam;
the first beam propagates along a first direction and the second beam propagates along a second direction, and the first direction and the second direction extend at an angle to the rod axis;
the analytical detector is arranged along the first direction;
the reference detector is arranged along the second direction;
the analytical filter is arranged between the analytical detector and the outlet end and;
the reference filter is arranged between the reference detector and the outlet end.

5. A gas detector system in accordance with claim 4, wherein the analytical filter and the reference filter are designed as bandpass filters, whose transmission ranges differ from one another.

6. A gas detector system in accordance with claim 4, further comprising a receiver light source arranged on a side of the outlet end pointing away from the receiver lens assembly on the receiver axis.

7. A gas detector system in accordance with claim 6, wherein the transmitter further comprises a filter arranged between the transmitter lens assembly and the light source and reflecting light falling on the transmitter lens assembly against the emission direction onto a position-sensitive detection means provided in the transmitter.

8. A gas detector system in accordance with claim 1, wherein:
the light mixing rod has a circumferential wall extending between the inlet end and the outlet end;
light-sensitive sensor diodes, are arranged on the circumferential wall at spaced locations from one another in the circumferential direction; and
the light-sensitive area of the sensors points towards the interior of the light mixing rod.

9. A gas detector system in accordance with claim 8, wherein the light mixing rod has a polygonal cross section as viewed at right angles to the rod axis.

10. A gas detector system in accordance with claim 1, wherein:
the light mixing rod is a first light mixing rod, the inlet end is a first inlet end, the outlet end is a first outlet end and the rod axis is a first rod axis extending from the first inlet end to the first outlet end;
the receiver defines a second light mixing rod, which has a second inlet end and a second outlet end, and a second rod axis extending from the second inlet end to the second outlet end;
the second inlet end is arranged closer to the receiver lens assembly than the first inlet end, as viewed in the direction of a beam falling into the receiver;
the first and second rod axes extend at an angle to one another;
the reference detector is arranged on the side of the second outlet end pointing away from the receiver lens assembly as viewed in the direction of a beam falling into the receiver;
the analytical filter is arranged between the first inlet end and the receiver lens assembly;
the analytical filter is aligned such that light that falls on the analytical filter along the receiver axis and is not transmitted is reflected along the second rod axis onto the second inlet end; and
the reference filter is arranged between the receiver lens assembly and the analytical filter.

11. A gas detector system in accordance with claim 10, wherein:
the first rod axis extends along the receiver axis; and
the second rod axis extends at an angle to the receiver axis.

12. A gas detector system in accordance with claim 10, wherein the reference filter is aligned such that light that falls on the reference filter along the receiver axis and is not transmitted is reflected onto a second position-sensitive detection means provided in the receiver.

13. A gas detector system in accordance with claim 10, wherein the optical path lengths between the receiver lens assembly and the first light rod and between the receiver lens assembly and the second light mixing rod are selected to be such that the focal point is located within the first and second light mixing rods.

14. A gas detector system in accordance with claim 10, wherein:
the reference filter is designed as a bandpass filter;
the analytical filter is designed as a cut-off filter and
the lower threshold wavelength of the bandpass filter is lower than the cut-off wavelength.

15. A gas detector system in accordance with claim 10, wherein the first and/or second light mixing rod is designed such that it conically tapers towards the outlet end.

16. A gas detector system in accordance with claim 12, wherein the first and/or second position-sensitive detection means is designed as a CCD, CMOS or quadrant detector.

* * * * *